United States Patent [19]

Cosgrove et al.

[11] Patent Number: 5,350,420
[45] Date of Patent: * Sep. 27, 1994

[54] FLEXIBLE ANNULOPLASTY RING AND HOLDER

[75] Inventors: Delos M. Cosgrove, Hunting Valley, Ohio; Than Nguyen, Huntington Beach, Calif.

[73] Assignee: Baxter International Inc., Deerfield, Ill.

[*] Notice: The portion of the term of this patent subsequent to Aug. 20, 2008 has been disclaimed.

[21] Appl. No.: 68,279

[22] Filed: May 25, 1993

Related U.S. Application Data

[63] Continuation of Ser. No. 833,600, Feb. 10, 1992, abandoned, which is a continuation of Ser. No. 387,909, Jul. 31, 1989, abandoned.

[51] Int. Cl.⁵ .............................................. A61F 2/24
[52] U.S. Cl. ............................................ 623/2; 623/900
[58] Field of Search ................ 623/2, 900; 606/1, 153

[56] References Cited

U.S. PATENT DOCUMENTS

| | | | |
|---|---|---|---|
| 3,656,185 | 4/1972 | Carpentier | 623/2 |
| 3,828,787 | 8/1974 | Anderson et al. | 623/2 |
| 4,042,979 | 7/1977 | Angell | 623/2 |
| 4,055,861 | 11/1977 | Carpentier et al. | 623/2 |
| 4,164,046 | 7/1979 | Cooley | 623/2 |
| 4,204,283 | 5/1980 | Bellhouse et al. | 623/2 |
| 4,290,151 | 9/1981 | Massana | 623/2 |
| 4,306,319 | 12/1981 | Kaster | 623/2 |
| 4,364,126 | 12/1982 | Rosen et al. | 623/2 |
| 4,489,446 | 12/1984 | Reed | 623/2 |
| 4,585,453 | 4/1986 | Martin et al. | 623/2 |
| 4,602,911 | 7/1986 | Ahmadi et al. | 623/2 |
| 4,655,218 | 4/1987 | Kulik et al. | 623/2 |
| 4,743,253 | 5/1988 | Magladry | 623/2 |
| 4,750,492 | 6/1988 | Jacobs | 606/230 |
| 4,759,758 | 7/1988 | Gabbay | 623/2 |
| 4,865,600 | 9/1989 | Carpentier et al. | 623/2 |
| 5,011,481 | 4/1991 | Myers et al. | 606/1 |
| 5,041,130 | 8/1991 | Cosgrove et al. | 623/2 |

FOREIGN PATENT DOCUMENTS

| | | |
|---|---|---|
| 3560971 | 5/1973 | Australia ......................... 623/2 |
| A20200419 | 11/1986 | European Pat. Off. . |
| A20242172 | 10/1987 | European Pat. Off. . |
| WO 87/5489 | 9/1987 | PCT Int'l Appl. . |
| A2083362 | 3/1982 | United Kingdom . |

OTHER PUBLICATIONS

Grismer et al. "A Suture Holder and Separater Attachment to the Starr-Edwards Prosthetic Valve Holders" *Surg. Gyn. and Obst.* Mar., 1965 pp. 583-584 623-2.

"Clinical and Hemodynamic Performance of a Totally Flexible Prosthetic Ring for Atrioventricular Valve Reconstruction" Duran, Ubago; The Annals of Thoracic Surgery; vol. 22, No. 5; pp. 248-463.

"Conservative Surgery of the Mitral Valve. Annuloplasty on a New Adjustable Ring"; Massana, Calbet and Castells; Cardio. Surg. 1980.

*Primary Examiner*—David Isabella
*Assistant Examiner*—Elizabeth M. Burke
*Attorney, Agent, or Firm*—Raymond Sun; Debra Condino

[57] ABSTRACT

An assembly for holding a substantially flexible annuloplasty ring in a substantially taunt position for suturing about a valve annulus. The assembly includes a portion which is formed with a surface against which the annuloplasty ring is positioned and held in a shape substantially equivalent to at least a portion of the valve annulus. The assembly further includes a mechanism for releasably binding the annuloplasty ring to this surface.

16 Claims, 3 Drawing Sheets

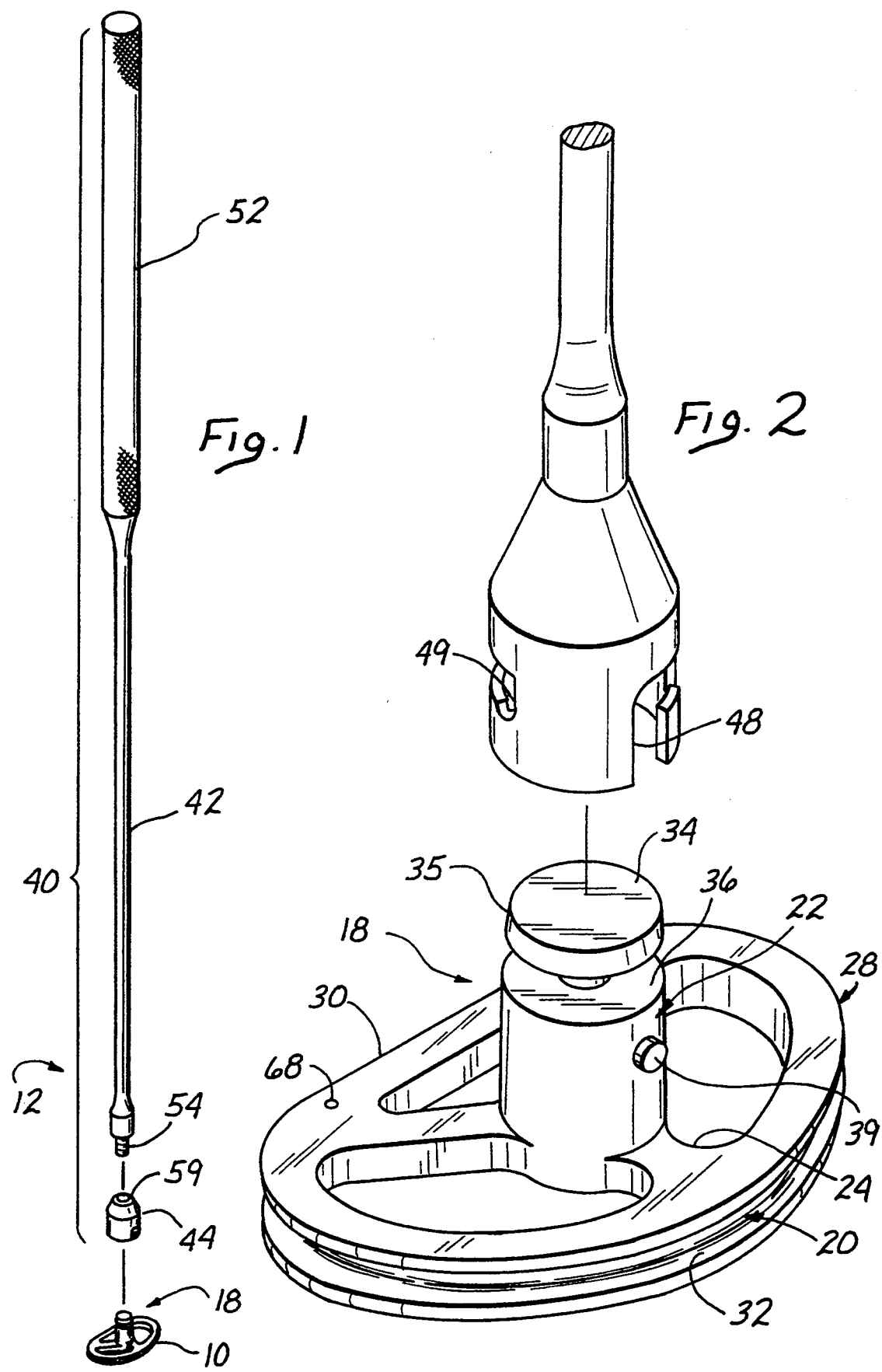

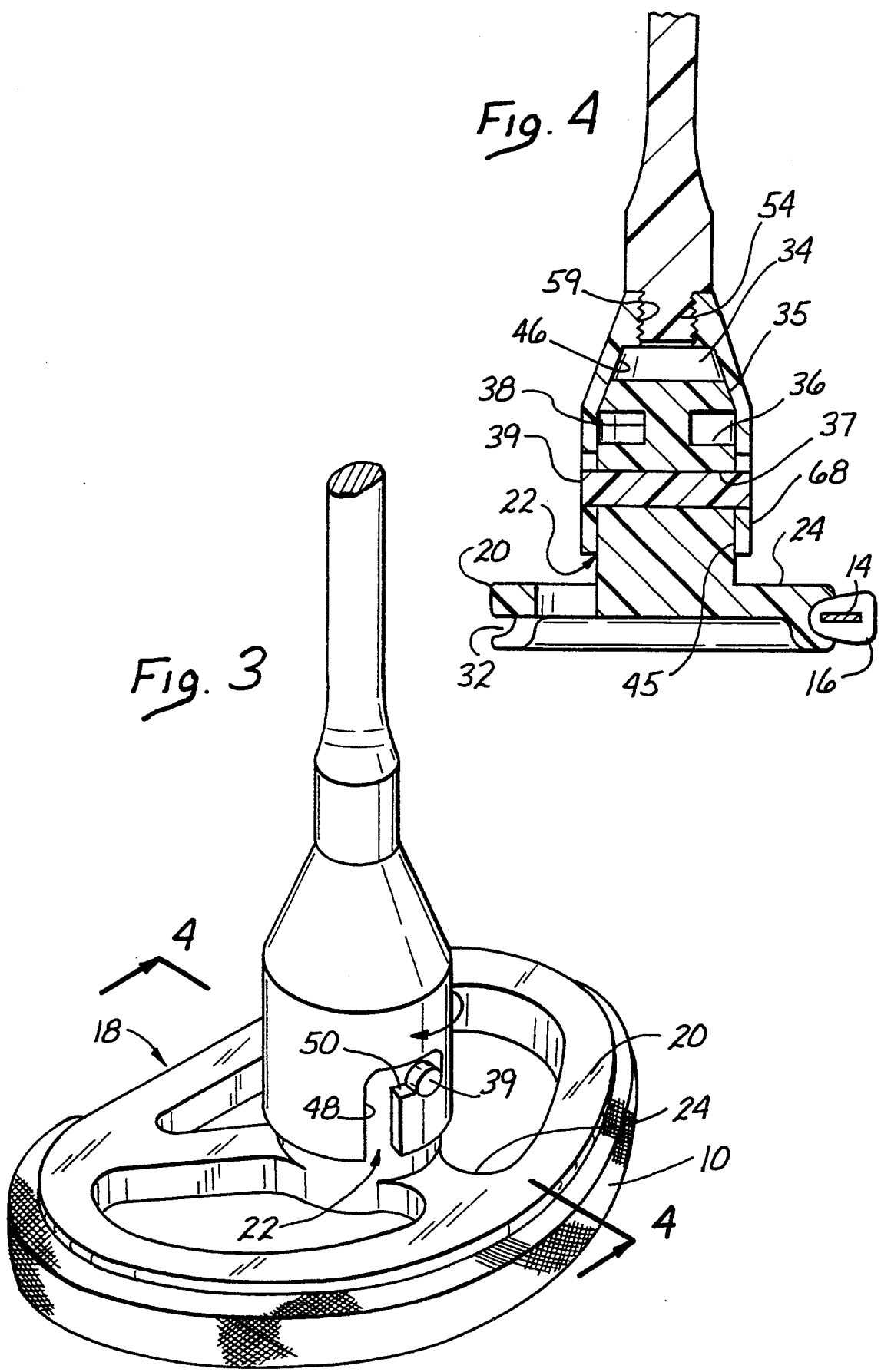

FLEXIBLE ANNULOPLASTY RING AND HOLDER

This is a continuation of application Ser. No. 07/833,600 filed on Feb. 10, 1992, now abandoned which is a continuation of application Ser. No. 07/387,909 filed on Jul. 31, 1989, now abandoned.

BACKGROUND OF THE INVENTION

The present invention relates to a support for a natural human heart which may be used for the surgical correction of a deformed heart valve, specifically a heart valve which has become dilated. In particular, the present invention relates to a holder and flexible annuloplasty ring prosthesis combination for properly positioning the ring about the valve annulus during implantation.

The human heart generally includes four valves. Of these valves the more critical ones are known as the mitral valve, which is located in the left atrioventricular opening, and the tricuspid valve, which is located in the right atrioventricular opening. Both of these valves are intended to prevent regurgitation of blood from the ventricle into the atrium when the ventricle contracts. In preventing blood regurgitation both valves must be able to withstand considerable back pressure as the ventricle contracts. The valve cusps are anchored to the muscular wall of the heart by delicate but strong fibrous cords in order to support the cusps during ventricular contraction. Furthermore, the geometry of the heart valves ensure that the cusps overlay each other to assist in control ling the regurgitation of the blood during ventricular contraction.

Diseases and certain natural defects to heart valves can impair the functioning of the cusps in preventing regurgitation. For example, certain diseases cause the dilation of the heart valve annulus. Dilation may also cause deformation of the valve geometry or shape displacing one or more of the valve cusps from the center of the valve. Other diseases or natural heart valve defects result in deformation of the valve annulus with little or no dilation.

Dilation and/or deformation result in the displacement of the cusps away from the center of the valve. This results in an ineffective closure of the valve during ventricular contraction, which results in the regurgitation or leakage of blood during ventricle contraction. For example, diseases such as rheumatic fever or bacterial inflammations of the heart tissue can cause distortion or dilation of the valvular annulus. Other diseases or malformations result in the distortion of the cusps, which will also lead to ineffective closure of the valve.

One method of repairing an impaired valve is to completely replace the valve. This method is particularly suitable for replacing a heart valve when one of the cusps has been severely damaged or deformed. While the replacement of the entire valve eliminates the immediate problem associated with a dilated valve annulus, presently available heart valves do not possess the same durability as natural heart valves. Various surgical procedures have been developed to correct the deformation of the valve annulus and retain the intact natural heart valve.

These surgical techniques involve repairing the shape of the dilated or elongated valve. Such techniques, generally Known as annuloplasty, require surgically restricting the valve annulus to minimize dilation. Typically, a prosthesis is sutured about the base of the valve leaflets to reshape the valve annulus and restrict the movement of the valve annulus during the opening and closing of the valve.

A suitable prosthesis should allow the surgeon to properly reconstruct the heart valve annulus and minimize dilation, while allowing natural movement of the valve annulus during the opening and closing of the valve. The ability of the prosthesis to allow for a natural opening and closing of the valve is particularly important since such prostheses are not normally removed from the heart valve, even if the valve annulus heals to a normal geometry.

Many different types of prostheses have been developed for use in annuloplasty surgery. In general prostheses are annular or partially annular shaped members which fit about the base of the valve annulus. Initially the prostheses were designed as rigid frame members, to correct the dilation and reshape the valve annulus to the natural state. These annular prostheses were formed from a metallic or other rigid material, which flexes little, if at all, during the normal opening and closing of the valve.

Examples of rigid annuloplasty ring prostheses are disclosed in U.S. Pat. Nos. 3,656,185, issued to Carpentier on Apr. 18, 1972; and 4,164,046, issued to Cooley on Aug. 14, 1979. Certain artificial heart valves have also been developed with rigid frame members similar to the rigidity of the described valve prosthesis. Examples of this type of heart valve are disclosed in U.S. Pat. Nos. 4,204,283, issued to Bellhouse et al on May 27, 1980; and 4,306,319, issued to Kaster on Dec. 22, 1981.

Rigid annuloplasty ring prostheses adequately promote the healing of the valve annulus by restricting valve dilation and reshaping the valve annulus. However, this rigidity prevents the normal flexibility of the valve annulus. That is, a normal heart valve annulus continuously flexes during the cardiac cycle, and a rigid ring prosthesis interferes with this movement. Since the prosthesis remains implanted, even after the valve annulus has healed, a prosthesis of high rigidity will permanently restrict the normal opening and closing of the valve, and thus impair the normal functioning of the valve. Another disadvantage with a highly rigid ring prosthesis is the tendency of the sutures tearing during the normal movement of the valve annulus.

Other workers have suggested the use of completely flexible annuloplasty ring prostheses. Flexible prostheses include an inner support member formed from a flexible material. This support member is wrapped in woven, biocompatible cloth material. Resistance to the dilation of the annulus during the opening and closing of the valve is obtained by the proper suturing of the ring about the valve annulus.

One disadvantage with completely flexible ring prostheses is that during the implantation process the material forming the ring may become bunched at localized areas. This bunching of the prosthesis results in the phenomenon known as multiple plications of the ring prosthesis. One result of this phenomenon is variability of the ability of the ring to control the shape of the valve annulus. The bunched up areas of the ring tend to provide a more rigid area in comparison to the other portions of the ring which results in distorting the valve annulus during the opening and closing of the valve.

Examples of completely flexible ring prostheses are disclosed in U.S. Pat. No. 4,290,151, issued to Massana on Sep. 22, 1981, and are discussed In the articles of Carlos D. Duran and Jose Luis M. Ubago, "Clinical and Hemodymanic Performance of a Totally Flexible Prosthetic Ring for Atrioventricular Valve Reconstruction", 5 Annals of Thoracic Surgery, (No. 5), 458–463, (Nov. 1976) and M. Puig Massana et al, "Conservative Surgery of the Mitral Valve Annuloplasty on a New Adjustable Ring", Cardiovascular Surgery 1980, 30–37, (1981).

Still further types of annuloplasty ring prostheses are designed to allow for adjustment of the ring circumference, either during the surgical implantation, or as the ring prosthesis during the opening and closing of the valve. This type of adjustable prosthesis is typically designed in combination with a rigid, or at least partially rigid frame member.

An example of a self adjusting ring prosthesis is taught in U.S. Pat. No. 4,489,446, issued to Reed on Dec. 25, 1984. This annuloplasty ring prosthesis provides for self adjustment of the prosthesis annulus by two reciprocating pieces which form the prosthesis frame. The basic disadvantage of this ring prosthesis is that the individual frame members are formed from a rigid material, with the resulting prosthesis suffering the same disadvantages discussed above for rigid ring prosthesis in general.

Other examples of adjustable ring prostheses are taught in U.S. Pat. Nos. 4,602,911, issued to Ahmadi et al and 4,042,979, issued to Angell on Aug. 23, 1977, provide for mechanism of adjusting the ring circumference. In Ahmadi et al the ring prosthesis frame is a coiled spring ribbon which is adjusted by a mechanical screw assembly. In Angell, a drawstring is used to adjust the circumference of a rigid frame member. Again, these ring prostheses suffer from the disadvantages of the rigid ring prosthesis discussed above. The Angell prosthesis could also possess a substantially flexible portion after suturing which could include multiple plications for the reasons discussed above for the completely flexible prosthesis.

U.S. Pat. No. 4,055,861, issued to Carpentier on Nov. 1, 1977 teaches an annuloplasty ring prosthesis which has a flexibility between the completely flexible rings discussed above and rigid ring. The ring of Carpentier is deformable to an equal degree and simultaneously in all directions. The preferred support is described as having the elasticity of an annular bundle of 2 to 8 turns of a cylindrical bristle of poly(ethylene terephthalate).

While rigid and semi-rigid annuloplasty rings provide a benefit over flexible rings, the restrictive nature of such rings may be detrimental to the ability of the valve to normally open and close. It thus remains an object to provide a flexible annuloplasty ring which does not have the any of the above described detriments.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 1 is a prospective exploded view of a annuloplasty ring prosthesis and holder assembly in accordance with an embodiment of the invention;

FIG. 2 is an exploded view of the ring mount portion and lower part of the handle portion of the holder assembly of FIG. 1;

FIG. 3 is a prospective view of the assembled ring mount and lower handle portions seen in FIG. 2;

FIG. 4 is a cross sectional view of the assembled ring mount and lower handle portions of FIG. 3 along line 4—4;

SUMMARY OF THE INVENTION

Figure 5:
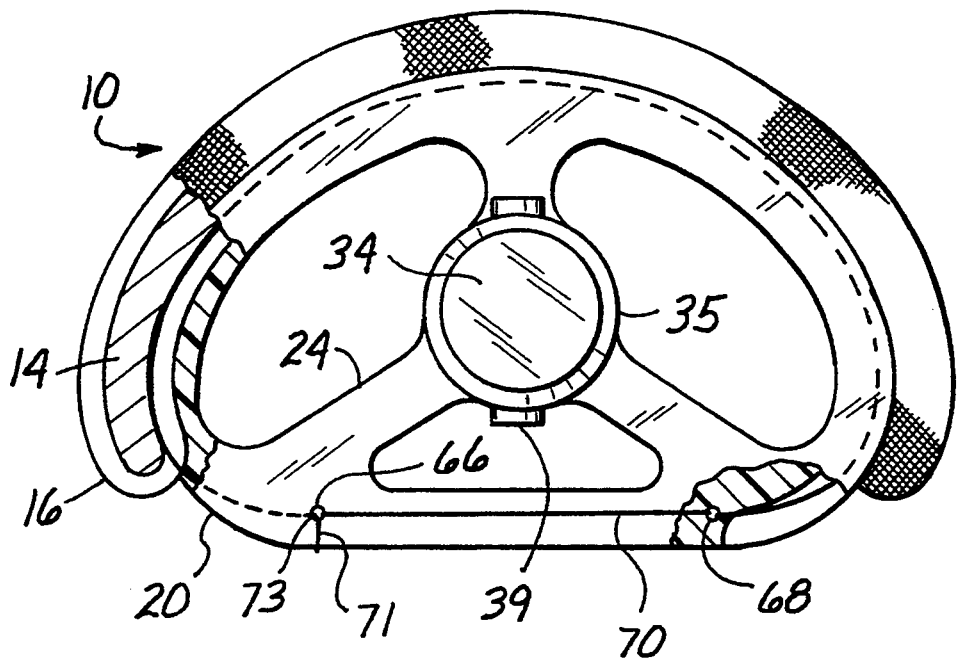
FIG. 5 is a top view of the ring mount seen in FIGS. 2–4 with a flexible annuloplasty secured thereto.

The present invention overcomes the above discussed disadvantages by providing an assembly for holding a substantially flexible annuloplasty ring in a substantially taut position for suturing about a valve annulus. The assembly includes a portion which is formed with a surface against which the annuloplasty ring is positioned and held in a shape substantially equivalent to at least a portion of the valve annulus. The assembly further includes a mechanism for releasably binding the annuloplasty ring this surface.

The annuloplasty ring prosthesis used with the assembly of the invention is a generally elongated flexible body element formed from an internal flexible frame wrapped in a woven cloth material.

The holder assembly includes a body which is formed with an outwardly facing surface against which is positioned the annuloplasty ring. This surface is dimensioned with a shape substantially similar to at least a portion of valve annulus. Preferably, this surface is formed with at least one depression for receiving a portion of the ring prosthesis.

The annuloplasty ring prosthesis is releasably retained against the body surface by at least a first thread. This thread is affixed at both ends to the body with a portion thereof passing at least partially through the annuloplasty ring prosthesis. The thread is affixed to the body to expose a portion which when disected subdivides the thread into two pieces affixed at one end to the body. At least one of these pieces defines that portion passing through the ring prosthesis and which is freely withdrawn from the annuloplasty ring.

DESCRIPTION OF THE PREFERRED EMBODIMENTS

The present invention is directed to a holder assembly for holding a substantially flexible annuloplasty ring in a substantially taut position for suturing about a valve annulus. The prosthesis of the invention is formed from a flexible body about which a woven cloth is wrapped to form a covering. The annuloplasty ring prosthesis of the invention is surgically sutured, with the aid of the holder assembly, to the annulus of a dilated and/or deformed heart valve. The dilation and/or deformation of heart valves may be the result of a disease, natural defect or physical damage to the valve annulus. This dilated and/or deformed heart valve will not completely close, allowing for regurgitation of blood with a closed valve.

The suturing of the prosthesis to the valve annulus restricts the circumference of the dilated valve to a more natural dimension. The prosthesis of the invention thus restrains dilation of the valve and al lows the surgeon to reshape the valve.

The holder assembly includes a ring mount assembly about which the annuloplasty ring is mounted and releasably affixed. Generally the ring mount assembly includes a ring support which formed with a shape similar to that of the valve annulus about which the annuloplasty ring is to be implanted. The annuloplasty ring is mounted about a portion of this ring support, typically about a curved portion. The holder assembly allows the surgeon to properly position the annuloplasty ring during the suturing process, and minimize the potential of forming multiple plications as the ring prosthesis is sutured in position.

Referring now to FIG. 1, an exploded view of a holder assembly to which an annuloplasty ring is mounted, as seen generally at 12 and 10 respectively. The holder assembly 12 includes a ring mount assembly 18 and handle assembly 40, which is formed from a handle 42 and housing 44.

The annuloplasty ring prosthesis 10 is a generally straight member formed with an inner frame 14 about which is wrapped an outer cloth 16, as better seen in FIGS. 4 and 5. Frame 14 is formed from a flat or tubular piece of resilient, flexible material, e.g. mylar, with the outer cloth 16 formed from any biocompatible, woven cloth material is adequate for use as the outer cloth 16. Preferably, the outer cloth 16 is dacron. This outer cloth 16 is tightly wrapped and sewen about this frame 14 The thickness of the outer cloth 16 is sufficient to allow the surgeon to pass a suture therethrough.

As seen in FIGS. 2 through 5, the ring prosthesis 10 is mounted about the lower portion of the holder assembly 12. This portion of the holder assembly 12 is the ring mount assembly 18. Ring mount assembly 18 includes a ring support 20. This ring support 20 is generally annular, with a shape similar to that of the annulus of the valve to which the ring prosthesis 10 is being sutured. More particularly, ring support 20 has a C-shaped portion 28, with its ends connected by a straight side 30.

The ring prosthesis 10 is fitted about the curved C-shaped portion 28 of the ring support 20. The ring support 20 is formed with a groove or trough 32 which is dimensioned to receive a portion of the ring prosthesis 10, as best seen in FIG. 4. The positioning of the ring prosthesis 10 within the trough 32 slightly deforms the ring prosthesis 10. This deformation places a thicker portion of the woven cloth 16 outside of the trough 32 to allow the surgeon to pass a suture therethrough.

The ring mount assembly 18 also includes a central support hub 22 to which the ring support 20 is attached by three integrally formed spokes, one of which is seen at 24. The arrangement allows the surgeon to visual observe the heart valve during the suturing process. Central support hub 22 is formed with an annular groove 36. This groove 36 is formed proximate that end 34 of hub 22 opposite ring support 20, and defines a post member 38. That portion of hub 22 remaining at that side of the groove 36 opposite the ring support 20, hub end 34, includes an inwardly tapering peripheral surface, as seen generally at 35. The hub 22 is also includes an open bore 37 through which is fitted a cylindrical plug 39. The plug 39 is dimensioned to extend out from both sides of the bore 37. The purpose of tapered surface 35, and the plug 39 will be described in greater detail herein.

As stated the handle assembly 40 includes an elongated post 42 and a housing 44. As seen in FIG. 1, housing 44 is mounted to an end 54 of post 42. While the housing 44 may be integrally formed at the end 54 of the post 42, preferably end 54 is formed with outwardly facing threads. These threads are formed to threadably mate with threads formed along a surface of an opening formed on the top of the housing 44, seen generally at 59. The opposite end of the post 42 Is formed with an external etched surface 52. This etched surface 52 assists the surgeon in gripping post 42.

Housing 44 Is a thimble shaped structure having a circular wall 60 which defines a cavity 46. As seen better in FIG. 4, cavity 46 is open at one side, seen generally as opening 45. The inner surface of the circular wall 60 inwardly converges a short distance from the opening 45. The cavity 46 is generally wide enough at the open side 45 to snuggly receive hub 22, but the plug 39 extends sufficiently outward from hub 22 to prevent passage through open side 45 into cavity 46. Hall 60 is formed with two J-shaped notches, seen at 48 and 49 in FIGS. 2 and 3. These J-shaped notches 48 and 49 are formed and positioned to respectively receive the ends of the plug 39 extending outward from the hub 22. The shape of the notches 48 and 49 defines a landing 50 between the long and short legs of each notch.

Handle assembly 40 is coupled to the ring mount assembly 18 by inserting end 54 of the hub 22 into the cavity 46, with the outwardly extending ends of the plug 39 passing through a respective on of each J-shaped notche 48 and 49. The tapered surface 35 of the hub 22 engages the inwardly tapering surface of the wall 60. This causes a slight compression of the hub end 34, resulting in a spring force. The spring force acts to restrain the movement of the outwardly extending ends of the plug 39 through the larger legs of the J-shaped notches 48 and 49. Additional exertion moves the plug 39 ends through the larger legs of J-shaped notches 48 and 49, with rotation of the handle 40 passing the outward ends of the plug 39 across the landings 50 and into the smaller leg of each J-shaped notch 48 and 49.

The spring force established by the slight compression of the hub end 54 maintains the assembly of the housing 44 and ring mount assembly 18. The handle 40 is decoupled from the ring mount assembly 18 by reversing the described procedure.

The mechanism for attaching the ring prosthesis 10 to the ring support 20 of the ring mount assembly 18 is seen in FIG. 5. Ring support 20 is formed with two holes 66 and 68. Each of the holes 66 and 68 is formed through the ring support 20 and communicates with the groove 32. The exact positioning of the holes 66 and 68 is not critical. As illustrated these holes 66 and 68 are formed along the straight portion of the ring support 20, at a location proximate two of the spokes 24.

One end 71 of a cord or suture 70 is passed through one of the holes, as illustrated hole 66, and tied off on the ring support 20. The other end 73 of suture 70 is passed through the body of ring prosthesis 10 from one end to the other. This end 73 is then passed first through hole 68 and then through and tied off at hole 66. After the ring prosthesis 10 is sutured in position about the valve annulus, that portion of the suture 70 between the two holes 66 and 68 is sniped. The suture 70 passes out of the ring prosthesis 10 by withdrawing the handle assembly 12.

In accordance with another embodiment, the first end 71 is tied off at hole 66, with the second end 73 passed first through one end of the ring prosthesis 10, and then brought back across and passed through the other prosthesis 10 end. This suture end 73 is again tied off at hole 66. Removal of suture 70 is accomplished by sniping the suture between the two holes.

Figure 6:
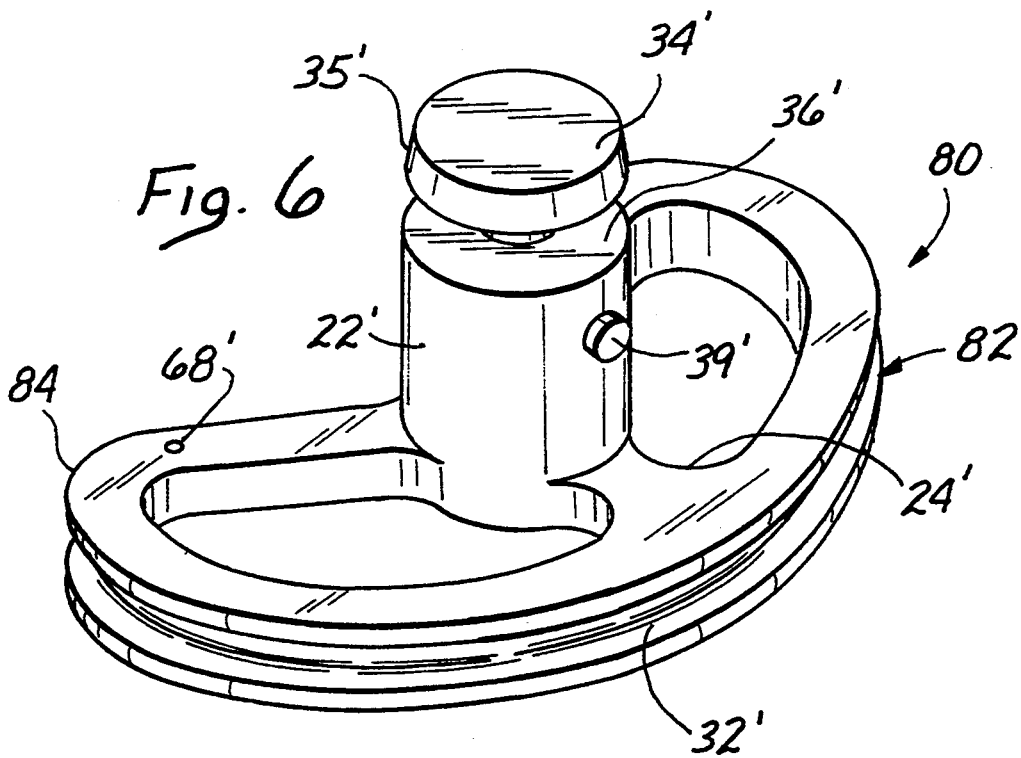
FIG. 6 is a prospective view of a ring mount in accordance with another embodiment of the invention.

The above described ring mount assembly 18 includes a ring support 20 formed by a C-shaped and straight side as best seen in FIG. 5. A second embodiment is seen in FIG. 6. This ring mount assembly 80 includes a ring support 82 which is formed with only an open C-shaped side 84. Except for the stated difference in shape of the ring support 82, this ring mount assembly 80 includes similar elements as those described for ring support 20, which are indicated by the prime of the previously provided element number, and will not be described in any more detail herein. This embodiment of ring mount assembly 80 provides an open area across which a suture is positioned after being tied off at the respective hole 66.

While the preferred embodiments have been described, various modifications and substitutions may be made thereto without departing from the scope of the invention. Accordingly, it is to be understood that the invention has been described by way of illustration and not limitation.

What is claimed is:

1. An assembly useful for holding an annuloplasty ring in a substantially taut position for suturing about a valve annulus comprising:
   a holder body comprising groove means formed with a circumferential surface for receiving an annuloplasty ring; and
   releasable retaining means for tautly holding an annuloplasty ring against said groove means circumferential surface, said releasable retaining means being operable to selectively release an annuloplasty ring from said holder body groove means.

2. The assembly of claim 1 wherein said holder body includes:
   handle means which is coupled to said holder body and formed to be gripped during the implantation of an annuloplasty ring.

3. The assembly of claim 2 wherein said handle means is releasably connected to said holder body.

4. The assembly of claim 2 wherein said holder body groove means circumferential surface is an outwardly facing channel for at least partially receiving an annuloplasty ring.

5. The assembly of claim 4 wherein said releasable retaining means is at least a first thread having two opposing ends for selectively attaching at least a portion of an annuloplasty ring to said holder body.

6. The assembly of claim 4 wherein said releasable retaining means includes at least a first thread having opposing ends, at least a portion of said first thread adapted to be passed through or around a portion of an annuloplasty ring, with both of said ends being affixed to said holder body, said thread being affixed to said holder body to expose a portion of said thread which when cut allows said thread to be freely withdrawn as at least one segment from an annuloplasty ring while remaining attached to said holder body.

7. The assembly of claim 2 wherein said releasable retaining means is at least a first thread having two opposing ends for selectively attaching an annuloplasty ring to said holder body.

8. The assembly of claim 2 wherein said releasable retaining means includes at least a first thread having opposing ends, at least a portion of said first thread adapted to be passed through or around a portion of an annuloplasty ring, with both of said ends being affixed to said holder body, said thread being affixed to said holder body to expose a portion of said thread which when cut allows said thread to be freely withdrawn as at least one segment from an annuloplasty ring while remaining attached to said holder body.

9. The assembly of claim 1 wherein said releasable retaining means includes at least a first thread having opposing ends, at least a portion of said first thread adapted to be passed through or around a portion of an annuloplasty ring, with both of said ends being affixed to said holder body, said thread being affixed to said holder body to expose a portion of said thread which when cut allows said thread to be freely withdrawn as at least one segment from an annuloplasty ring while remaining attached to said holder body.

10. An annuloplasty ring and holder assembly combination comprising:
    an annuloplasty ring;
    a holder means for holding said annuloplasty ring in a substantially taut position for suturing about a valve annulus, said holder means including a body formed with groove means having a circumferential surface against which said annuloplasty ring is positioned; and
    a releasable retaining means for tautly attaching said annuloplasty ring against said holder groove means circumferential surface, said releasable retaining means being selectively operable to release said annuloplasty ring from said holder means.

11. The combination of claim 10 wherein said releasable retaining means is at least a first thread having two opposing ends selectively attached to said holder means body and said annuloplasty ring.

12. The combination of claim 10 wherein said releasable retaining means includes at least a first thread having opposing ends, at least a portion of said first thread passing through a portion of said annuloplasty ring, with both of said thread ends being affixed to said holder means body to expose a portion of said thread which when cut allows said thread to be freely withdrawn, in at least one segment, from said annuloplasty ring while remaining attached to said holder means body.

13. An assembly useful for holding an annuloplasty ring in a substantially taut position for suturing about a valve annulus comprising:
    holder means comprising groove means formed with a circumferential surface for receiving an annuloplasty ring; and
    releasable retaining means for tautly holding an annuloplasty ring against said holder groove means circumferential surface, said releasable retaining means being selectively operable to release an annuloplasty ring from said holder groove means, said releasable retaining means includes at least a first thread having opposing ends, at least a portion of said first thread being passed through or around a portion of an annuloplasty ring and capable of being drawn to tautly hold an annuloplasty ring being received by said holder groove means with both of said thread ends being affixed to said holder means body to expose a portion, whereby cutting said thread allows said thread to be freely withdrawn, in at least one segment, from an annuloplasty ring while remaining attached to said holder groove means.

14. The assembly of claim 13 wherein said holder means further includes:
    handle means which is coupled to said holder means body and formed to be gripped during the implantation of an annuloplasty ring.

15. An annuloplasty ring and holder assembly combination comprising:

an annuloplasty ring;

a holder means for holding said annuloplasty ring in a substantially taut position for suturing about a valve annulus, said holder means including a body having groove means formed with a circumferential surface against which said annuloplasty ring is positioned; and a releasable retaining means for tautly attaching said annuloplasty ring against said holder groove means circumferential surface, said releasable retaining means being selectively operable to release said annuloplasty ring from said holder groove means, said releasable retaining means includes at least a first thread having opposing ends, at least a portion of said first thread passing through or around a portion of said annuloplasty ring, said first thread being drawn to tautly position said annuloplasty ring about said holder groove means circumferential surface with both of said thread ends being affixed to said holder groove means to expose a portion of said thread which when cut allows said thread to be freely withdrawn, in at least one segment, from said annuloplasty ring while remaining attached to said holder groove means.

16. The combination of claim 15 wherein said holder means further includes:

handle means which is coupled to said holder means body and formed to be gripped during the implantation of said annuloplasty ring.

* * * * *